United States Patent [19]

Maurer et al.

[11] 4,152,426
[45] May 1, 1979

[54] PESTICIDALLY ACTIVE O-ALKYL-O-[1,6-DIHYDRO-1-SUBSTITUTED-6-OXO-PYRIMIDIN-4-YL]-(THIONO)(THIOL) PHOSPHORIC (PHOSPHONIC) ACID ESTERS AND ESTER-AMIDES

[75] Inventors: Fritz Maurer; Hans-Jochem Riebel; Rolf Schröder, all of Wuppertal; Ingeborg Hammann, Cologne; Wolfgang Behrenz, Overath, all of Fed. Rep. of Germany

[73] Assignee: Bayer Aktiengesellschaft, Leverkusen, Fed. Rep. of Germany

[21] Appl. No.: 806,887

[22] Filed: Jun. 15, 1977

[30] Foreign Application Priority Data

Jul. 3, 1976 [DE] Fed. Rep. of Germany ....... 2630054

[51] Int. Cl.² .......................... A01N 9/36; C07F 9/65
[52] U.S. Cl. .................................. 424/200; 544/243; 544/298; 544/319
[58] Field of Search ....... 260/25 P, 256.4 E, 256.5 R; 424/200; 544/243

[56] References Cited

U.S. PATENT DOCUMENTS 3,862,188  1/1975  Milzner et al. ............... 260/251 P
4,045,561  8/1977  Mühle et al. ............... 260/251 P X
4,059,696 11/1977  Maurer et al. ............... 424/200

Primary Examiner—Donald G. Daus
Assistant Examiner—Diana G. Rivers
Attorney, Agent, or Firm—Sprung, Felfe, Horn, Lynch & Kramer

[57] ABSTRACT

O-alkyl-O-[1,6-dihydro-1-substituted-6-oxo-pyrimidin-4-yl]-(thiono)(thiol) phosphoric (phosphonic) acid esters and ester-amides of the formula

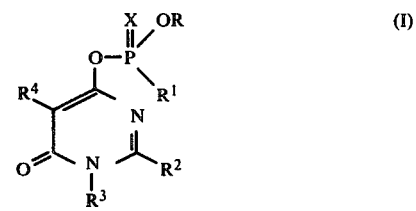

in which
R represents alkyl,
$R^1$ represents alkyl, alkoxy, alkylthio, monoalkylamino or phenyl,
$R^2$ represents hydrogen, alkyl, alkoxy, alkylthio or dialkylamino,
$R^3$ represents alkyl or alkenyl,
$R^4$ represents hydrogen, alkyl or halogen, and
X represents oxygen or sulphur, which possess insecticidal, acaricidal and nematicidal properties.

10 Claims, No Drawings

PESTICIDALLY ACTIVE O-ALKYL-O-[1,6-DIHYDRO-1-SUBSTITUTED-6-OXO-PYRIMID IN-4-YL]-(THIONO) (THIOL) PHOSPHORIC (PHOSPHONIC) ACID ESTERS AND ESTER-AMIDES

The present invention relates to and has for its objects the provision of particular new O-alkyl-O-[1,6-dihydro-1-substituted-6-oxo-pyrimidin-4-yl]-(thiono) (thiol) phosphoric (phosphonic) acid esters and esteramides which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from Swiss Patent Specification No. 321,868 and German Patent Specification No. 910,652 that certain O,O-dialkyl-O-pyrimidinyl-thionophosphoric acid esters, for example O,O-diethyl-O-[2-methylthio-(Compound A) or 2-isopropyl-6-methyl-pyrimidin-4-yl]-thionophosphoric acid ester (Compound B), have insecticidal and acaricidal properties.

The present invention now provides, as new compounds, the 6-oxo-pyrimidinyl(thiono)(thiol)-phosphoric(phosphonic) acid esters and ester-amides of the general formula

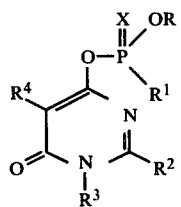
(I)

in which
R represents alkyl,
$R^1$ represents alkyl, alkoxy, alkylthio, monoalkylamino or phenyl,
$R^2$ represents hydrogen, alkyl, alkoxy, alkylthio or dialkylamino,
$R^3$ represents alkyl or alkenyl,
$R^4$ represents hydrogen, alkyl or halogen, and
X represents oxygen or sulphur.

Preferably, R represents straight-chain or branched alkyl with 1 to 4 carbon atoms, $R^1$ represents straight-chain or branched alkyl with 1 to 3 carbon atoms or straight-chain or branched alkoxy, alkylthio or monoalkylamino, each with 1 to 4 carbon atoms, or represents phenyl, $R^2$ represents hydrogen, straight-chain or branched alkyl with 1 to 4 carbon atoms, straight-chain or branched alkoxy or alkylthio, each with 1 to 3 carbon atoms, or dialkylamino with 1 to 3 carbon atoms per alkyl group, $R^3$ represents alkyl or alkenyl, each with up to 4 carbon atoms, $R^4$ represents hydrogen, chlorine, bromine, methyl or ethyl, and X represents sulphur.

Surprisingly, the 6-oxo-pyrimidinyl(thiono)(thiol)-phosphoric(phosphonic) acid esters and ester-amides according to the invention exhibit a better insecticidal, acaricidal and nematicidal action than the corresponding previously known O,O-dialkyl-O-pyrimidinylthionophosphoric acid esters of analogous structure and of the same type of action. The compounds according to the present invention thus represent a genuine enrichment of the art.

The invention also provides a process for the preparation of a 6-oxo-pyrimidinyl(thiono)(thiol)-phosphoric(phosphonic) acid ester or ester-amide of the formula (I) in which (a) a (thiono)(thiol)-phosphoric(phosphonic) acid ester halide or ester-amide halide of the general formula

(II), in which
R, $R^1$ and X have the above-mentioned meanings, and
Hal represents halogen, preferably chlorine, is reacted with a 1,6-dihydro-4-hydroxy-6-oxo-pyrimidine of the general formula

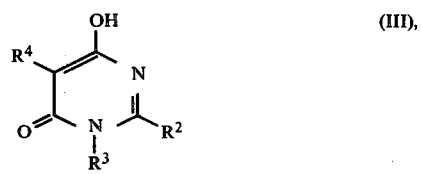
(III), in which
$R^2$, $R^3$ and $R^4$ have the above-mentioned meanings, if appropriate in the presence of an acid acceptor and, if appropriate, in the presence of a solvent, or (b) an O-[6-hydroxy-pyrimidin-4-yl]-(thiono)(thiol)-phosphoric(phosphonic) acid ester or ester-amide of the general formula

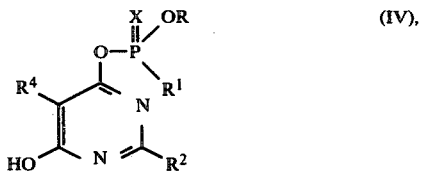
(IV), in which
R, $R^1$, $R^2$, $R^4$ and X have the above-mentioned meanings, is reacted with an alkyl halide or alkenyl halide of the general formula

in which
$R^3$ has the above-mentioned meaning and
$Hal^1$ represents halogen, preferably bromine or iodine, if appropriate in the presence of an acid acceptor and, if appropriate, in the presence of a solvent.

If, for example, O-ethyl-S-n-propyl-thionothiolphosphoric acid diester chloride and 5-chloro-1,6-dihydro-4-hydroxy-1-methyl-2-methylthio-6-oxo-pyrimidine or O-ethyl-S-n-propyl-O-[6-hydroxy-pyrimidin-4-yl]-thionothiolphosphoric acid ester and methyl iodide are used as starting materials, the course of the reactions can be represented by the following equations:

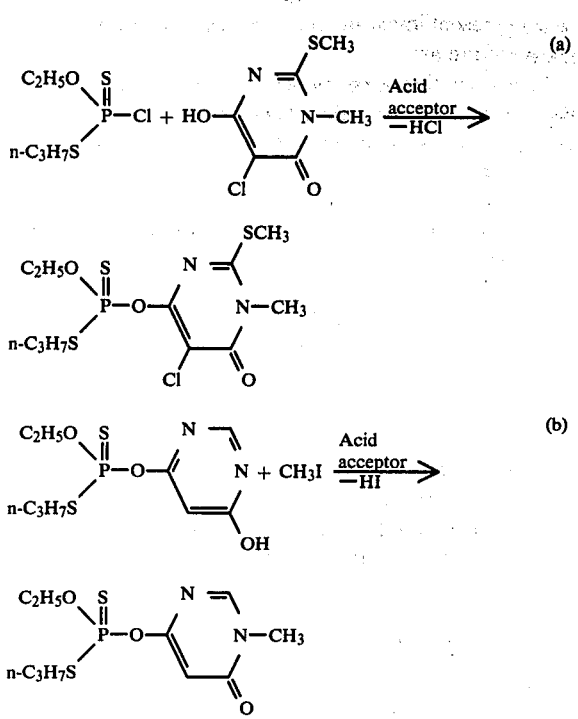

The (thiono)(thiol)-phosphoric(phosphonic) acid ester halides and acid ester-amide halides (II) to be used as starting materials are known and can be prepared in accordance with generally customary processes described in the literature. The following may be mentioned as individual examples of these compounds: O,O-dimethyl-, O,O-diethyl-, O,O-di-n-propyl-, O,O-di-isopropyl-, O,O-di-n-butyl-, O,O-di-isobutyl-, O,O-di-sec.-butyl-, O-methyl-O-n-propyl-, O-methyl-O-isopropyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-isopropyl-, O-ethyl-O-n-butyl-, O-ethyl-O-sec.-butyl-, O-ethyl-O-isobutyl-, O-n-propyl-O-butyl- and O-isopropyl-O-butyl-phosphoric acid diester chloride and the corresponding thiono analogues; O,S-dimethyl-, O,S-diethyl-, O,S-di-n-propyl-, O,S-di-isopropyl-, O,S-di-n-butyl-, O,S-di-isobutyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethylthiolphosphoric acid diester chloride and the corresponding thiono analogues; O-methyl-, O-ethyl-, O-n-propyl-, O-iso-propyl-, O-n-butyl-, O-iso-butyl-, O-sec.-butyl- and O-tert.-butyl-methane-, -ethane-, -n-propane-, -iso-propane-n-butane-, -isobutane-, -tert.-butane-, -sec.-butane- and -phenyl-phosphonic acid ester chloride and the corresponding thiono analogues; and O-methyl-N-methyl-, O-methyl-N-ethyl-, O-methyl-N-n-propyl-, O-methyl-N-isopropyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-isopropyl-, O-isopropyl-N-methyl-, O-isopropyl-N-ethyl-, O-iso-propyl-N-n-propyl-, O-isopropyl-N-isopropyl-, O-n-butyl-N-methyl-, O-n-butyl-N-ethyl-, O-n-butyl-N-n-propyl-, O-n-butyl-N-isopropyl-, O-tert.-butyl-N-methyl-, O-tert.-butyl-N-ethyl-, O-tert.-butyl-N-n-propyl-, O-tert.-butyl-N-iso-propyl-, O-iso-butyl-N-methyl-, O-isobutyl-N-ethyl-, O-sec.-butyl-N-methyl- and O-sec.-butyl-N-ethylphosphoric acid ester-amide chloride and the corresponding thiono analogues.

The 1,6-dihydro-4-hydroxy-6-oxo-pyrimidines (III) also to be used as starting materials can be prepared in accordance with processes known from the literature.

The following may be mentioned as individual examples of these compounds: 1-methyl-, 1-ethyl-, 1-n-propyl-, 1-iso-propyl-, 1-n-butyl-, 1-sec.-butyl-, 1-isobutyl-, 1-tert.-butyl-, 1-allyl-, 1-but-2-enyl- and 1-but-3-enyl- 1,6-dihydro-4-hydroxy-6-oxo-pyrimidine, as well as 1-methyl-5-chloro-, 1-methyl-5-bromo-, 1-methyl-5-methyl-, 1-methyl-5-ethyl-, 1-ethyl-5-chloro-, 1-ethyl-5-bromo-, 1-ethyl-5-methyl-, 1,5-diethyl-, 1-n-propyl-5-chloro-, 1-n-propyl-5-bromo-, 1-n-propyl-5-methyl-, 1-n-propyl-5-ethyl-, 1-isopropyl-5-chloro, 1-isopropyl-5-bromo-, 1-isopropyl-5-methyl-, 1-isopropyl-5-ethyl-, 1-n-butyl-5-bromo-, 1-n-butyl-5-chloro-, 1-n-butyl-5-methyl-, 1-n-butyl-5-ethyl-, 1-isobutyl-5-chloro, 1-isobutyl-5-bromo-, 1-isobutyl-5-methyl-, 1-isobutyl-5-ethyl-, 1-sec.-butyl-5-chloro-, 1-sec.-butyl-5-bromo-, 1-sec.-butyl-5-methyl-, 1-sec.-butyl-5-ethyl-, 1-allyl-5-bromo-, 1-allyl-5-chloro-, 1-allyl-5-methyl-, 1-allyl-5-ethyl-, 1-but-2-enyl-5-bromo-, 1-but-2-enyl-5-chloro-, 1-but-2-enyl-5-methyl- and 1-but-2-enyl-5-ethyl-1,6-dihydro-4-hydroxy-6-oxo-pyrimidine, 1,2-dimethyl-, 1-ethyl-2-methyl-, 1-n-propyl-2-methyl-, 1-isopropyl-2-methyl-, 1-n-butyl-2-methyl-, 1-isobutyl-2-methyl-, 1-sec.-butyl-2-methyl-, 1-allyl-2-methyl-, 1-but-2-enyl-2-methyl-, 1-but-3-enyl-2-methyl-, 1-methyl-2-ethyl-, 1,2-diethyl-, 1-n-propyl-2-ethyl-, 1-isopropyl-2-ethyl-, 1-n-butyl-2-ethyl-, 1-isobutyl-2-ethyl-, 1-sec.-butyl-2-ethyl-, 1-allyl-2-ethyl-, 1-but-2-enyl-2-ethyl-, 1-but-3-enyl-2-ethyl-, 1-methyl-2-n-propyl-, 1-ethyl-2-n-propyl-, 1,2-di-n-propyl-, 1-isopropyl-2-n-propyl-, 1-n-butyl-2-n-propyl-, 1-isobutyl-2-n-propyl-, 1-sec.-butyl-2-n-propyl-, 1-allyl-2-n-propyl-, 1-but-2-enyl-2-n-propyl-, 1-but-3-enyl-n-propyl-, 1-methyl-2-isopropyl-, 1-ethyl-2-isopropyl-, 1-n-propyl-2-isopropyl-, 1,2-di-isopropyl-, 1-n-butyl-2-isopropyl-, 1-isobutyl-2-isopropyl-, 1-sec.-butyl-2-isopropyl-, 1-allyl-2-iso-propyl-, 1-but-2-enyl-2-isopropyl-, 1-but-3-enyl-2-iso-propyl-, 1-methyl-2-n-butyl-, 1-ethyl-2-n-butyl-, 1-n-propyl-2-n-butyl-, 1-isopropyl-2-n-butyl-, 1,2-di-n-butyl-, 1-isobutyl-2-n-butyl-, 1-sec.-butyl-2-n-butyl-, 1-allyl-2-n-butyl-, 1-but-2-enyl-2-n-butyl-, 1-but-3-enyl-2-n-butyl-, 1-methyl-2-methoxy-, 1-ethyl-2-methoxy-, 1-n-propyl-2-methoxy-, 1-isopropyl-2-methoxy, 1-n-butyl-2-methoxy-, 1-iso-butyl-2-methoxy-, 1-sec.-butyl-2-methoxy-, 1-allyl-2-methoxy-, 1-but-2-enyl-2-methoxy-, 1-but-3-enyl-2-methoxy-, 1-methyl-2-ethoxy-, 1-ethyl-2-ethoxy-, 1-n-propyl-2-ethoxy-, 1-isopropyl-2-ethoxy-, 1-n-butyl-2-ethoxy-, 1-isobutyl-2-ethoxy-, 1-sec.-butyl-2-ethoxy-, 1-allyl-2-ethoxy-, 1-but-2-enyl-2-ethoxy-, 1-but-3-enyl-2-ethoxy-, 1-methyl-2-n-propoxy-, 1-ethyl-2-n-propoxy-, 1-n-propyl-2-n-propoxy-, 1-isopropyl-2-n-propoxy-, 1-n-butyl-2-n-propoxy-, 1-isobutyl-2-n-propoxy-, 1-sec.-butyl-2-n-propoxy-, 1-allyl-2-n-propoxy-, 1-but-2-enyl-2-n-propoxy-, 1-but-3-enyl-2-n-propoxy-, 1-methyl-2-iso-propoxy-, 1-ethyl-2-isopropoxy-, 1-n-propyl-2-iso-propoxy-, 1-isopropyl-2-isopropoxy-, 1-n-butyl-2-iso-propoxy-, 1-isobutyl-2-isopropoxy-, 1-sec.-butyl-2-iso-propoxy-, 1-allyl-2-isopropoxy-, 1-but-2-enyl-2-iso-propoxy-, 1-but-3-enyl-2-isopropoxy-, 1-methyl-2-methylthio-, 1-ethyl-2-methylthio-, 1-n-propyl-2-methylthio-, 1-isopropyl-2-methylthio-, 1-n-butyl-2-methylthio-, 1-isobutyl-2-methylthio-, 1-sec.-butyl-2-methylthio-, 1-allyl-2-methylthio-, 1-but-2-enyl-2-methylthio-, 1-but-3-enyl-2-methylthio-, 1-methyl-2-ethylthio-, 1-ethyl-2- ethylthio-, 1-n-propyl-2-ethylthio-, 1-isopropyl-2-ethylthio-, 1-n-butyl-2-ethylthio-, 1-isobutyl-2-ethylthio-, 1-sec.-butyl-2-ethylthio-, 1-allyl-2-ethylthio-, 1-but-2-enyl-2-ethylthio-, 1-but-3-enyl-2-ethylthio-, 1-methyl-2-n-propylthio-, 1-ethyl-2-n-propylthio-, 1-n-propyl-2-n-propylthio-, 1-isopropyl-2-n-propylthio-, 1-n-butyl-2-n-propylthio-, 1-isobutyl-2-n-propylthio-, 1-sec.-butyl-2-n-propylthio-, 1-allyl-2-n-propylthio-, 1-but-2-enyl-2-n-propylthio-, 1-but-3-enyl-2-n-propylthio-, 1-methyl-2-isopropylthio-, 1-ethyl-2-isopropylthio-, 1-n-propyl-2-isopropylthio-, 1-isopropyl-2-isopropylthio-, 1-n-butyl-2-isopropylthio-, 1-isobutyl-2-isopropylthio-, 1-sec.-butyl-2-isopropylthio-, 1-allyl-2-isopropylthio-, 1-but-2-enyl-2-isopropylthio-, 1-but-3-enyl-2-isopropylthio-, 1-methyl-2-dimethylamino-, 1-ethyl-2-dimethylamino-, 1-n-propyl-2-dimethylamino-, 1-isopropyl-2-dimethylamino-, 1-n-butyl-2-dimethylamino-, 1-isobutyl-2-dimethylamino-, 1-sec.-butyl-2-dimethylamino-, 1-allyl-2-dimethylamino-, 1-but-2-enyl-2-dimethylamino-, 1-but-3-enyl-2-dimethylamino-, 1-methyl-2-diethylamino-, 1-ethyl-2-diethylamino-, 1-n-propyl-2-diethylamino-, 1-isopropyl-2-diethylamino-, 1-n-butyl-2-diethylamino-, 1-isobutyl-2-diethylamino-, 1-sec.-butyl-2-diethylamino-, 1-allyl-2-diethylamino-, 1-but-2-enyl-2-diethylamino- and 1-but-3-enyl-2-diethylamino-1,6-dihydro-4-hydroxy-6-oxo-pyrimidine, as well as 1,2,5-trimethyl-, 1,2,5-triethyl-, 1-isopropyl-2-methyl-5-ethyl-, 1-isopropyl-2-methoxy-5-chloro-, 1-isopropyl-2-ethoxy-5-chloro-, 1-isopropyl-2-n-propoxy-5-chloro-, 1-isopropyl-2-methylthio-5-chloro-, 1-isopropyl-2-ethylthio-5-chloro-, 1-isopropyl-2-n-propylthio-5-chloro-, 1-isopropyl-2-isopropylthio-5-chloro-, 1-isopropyl-2-dimethylamino-5-chloro-, 1-isopropyl-2-diethylamino-5-chloro-, 1-isopropyl-2-methoxy-5-bromo-, 1-isopropyl-2-ethoxy-5-bromo-, 1-isopropyl-2-n-propoxy-5-bromo-, 1-isopropyl-2-methylthio-5-bromo-, 1-isopropyl-2-ethylthio-5-bromo-, 1-isopropyl-2-n-propylthio-5-bromo-, 1-isopropyl-2-isopropylthio-5-bromo-, 1-isopropyl-2-dimethylamino-5-bromo-, 1-isopropyl-2-diethylamino-5-bromo-, 1-isopropyl-2-methoxy-5-methyl-, 1-isopropyl-2-ethoxy-5-methyl-, 1-isopropyl-2-n-propoxy-5-methyl-, 1-isopropyl-2-methylthio-5-methyl-, 1-isopropyl-2-ethylthio-5-methyl-, 1-isopropyl-2-n-propylthio-5-methyl-, 1-isopropyl-2-iso-propylthio-5-methyl-, 1-isopropyl-2-dimethylamino-5-methyl-, 1-isopropyl-2-diethylamino-5-methyl-, 1-isopropyl-2-methoxy-5-ethyl-, 1-isopropyl-2-ethoxy-5-ethyl-, 1-isopropyl-2-n-propoxy-5-ethyl-, 1-isopropyl-2-methylthio-5-ethyl-, 1-isopropyl-2-ethylthio-5-ethyl-, 1-isopropyl-2-n-propylthio-5-ethyl-, 1-isopropyl-2-isopropylthio-5-ethyl-, 1-isopropyl-2-dimethylamino-5-ethyl-, 1-isopropyl-2-diethylamino-5-ethyl-, 1,5-diethyl-2-methyl-, 1-ethyl-2-methoxy-5-chloro-, 1-ethyl-2-ethoxy-5-chloro-, 1-ethyl-2-n-propoxy-5-chloro-, 1-ethyl-2-methylthio-5-chloro-, 1-ethyl-2-ethylthio-5-chloro-, 1-ethyl-2-n-propylthio-5-chloro-, 1-ethyl-2-isopropylthio-5-chloro-, 1-ethyl-2-dimethylamino-5-chloro-, 1-ethyl-2-diethylamino-5-chloro-, 1-ethyl-2-methyl-5-bromo-, 1-ethyl-2-methoxy-5-bromo-, 1-ethyl-2-ethoxy-5-bromo-, 1-ethyl-2-n-propoxy-5-bromo-, 1-ethyl-2-methylthio-5-bromo-, 1-ethyl-2-ethylthio-5-bromo-, 1-ethyl-2-n-propylthio-5-bromo-, 1-ethyl-2-isopropylthio-5-bromo-, 1-ethyl-2-dimethylamino-5-bromo-, 1-ethyl-2-diethylamino-5-bromo-, 1-ethyl-2,5-dimethyl-, 1-ethyl-2-methoxy-5-methyl-, 1-ethyl-2-ethoxy-5-methyl-, 1-ethyl-2-n-propoxy-5-methyl-, 1-ethyl-2-methylthio-5-methyl-, 1-ethyl-2-ethylthio-5-methyl-, 1-ethyl-2-n-propylthio-5-methyl-, 1-ethyl-2-isopropylthio-5-methyl-, 1-ethyl-2-dimethylamino-5-methyl-, 1-ethyl-2-diethylamino-5-methyl-1,5-diethyl-2-methoxy-, 1,5-diethyl-2-ethoxy-, 1,5-diethyl-2-n-propoxy-, 1,5-diethyl-2-methylthio-, 1,5-diethyl-2-ethylthio-, 1,5-diethyl-2-n-propylthio-, 1,5-diethyl-2-isopropylthio, 1,5-diethyl-2-dimethylamino-, 1,5-diethyl-2-diethylamino, 1-n-propyl-2-methyl-5-ethyl-, 1-n-propyl-2-methoxy-5-chloro-, 1-n-propyl-2-ethoxy-5-chloro-, 1-n-propyl-2-n-propoxy-5-chloro-, 1-n-propyl-2-methylthio-5-chloro-, 1-n-propyl-2-ethylthio-5-chloro-, 1-n-propyl-2-n-propylthio-5-chloro-, 1-n-propyl-2-isopropylthio-5-chloro-, 1-n-propyl-2-dimethylamino-5-chloro-, 1-n-propyl-2-diethylamino-5-chloro-, 1-n-propyl-2-methoxy-5-bromo-, 1-n-propyl-2-ethoxy-5-bromo-, 1-n-propyl-2-n-propoxy-5-bromo-, 1-n-propyl-2-methylthio-5-bromo-, 1-n-propyl-2-ethylthio-5-bromo-, 1-n-propyl-2-n-propylthio-5-bromo-, 1-n-propyl-2-isopropylthio-5-bromo-, 1-n-propyl-2-dimethylamino-5-bromo-, 1-n-propyl-2-diethylamino-5-bromo-, 1-n-propyl-2-methoxy-5-methyl-, 1-n-propyl-2-ethoxy-5-methyl-, 1-n-propyl-2-n-propoxy-5-methyl-, 1-n-propyl-2-methylthio-5-methyl-, 1-n-propyl-2-ethylthio-5-methyl-, 1-n-propyl-2-n-propylthio-5-methyl-, 1-n-propyl-2-iso-propylthio-5-methyl-, 1-n-propyl-2-dimethylamino-5-methyl-, 1-n-propyl-2-diethylamino-5-methyl-, 1-n-propyl-2-methoxy-5-ethyl-, 1-n-propyl-2-ethoxy-5-ethyl-, 1-n-propyl-2-n-propoxy-5-ethyl-, 1-n-propyl-2-methylthio-5-ethyl-, 1-n-propyl-2-ethylthio-5-ethyl-, 1-n-propyl-2-iso-propylthio-5-ethyl-, 1-n-propyl-2-dimethylamino-5-ethyl-, 1-n-propyl-2-diethylamino-5-ethyl-, 1-allyl-2-methyl-5-chloro-, 1-allyl-2-methoxy-5-chloro-, 1-allyl-2-ethoxy-5-chloro-, 1-allyl-2-n-propoxy-5-chloro-, 1-allyl-2-methylthio-5-chloro-, 1-allyl-2-ethylthio-5-chloro-, 1-allyl-2-n-propylthio-5-chloro-, 1-allyl-2-iso-propylthio-5-chloro-, 1-allyl-2-dimethylamino-5-chloro-, 1-allyl-2-diethylamino-5-chloro-, 1-allyl-2-methyl-5-bromo-, 1-allyl-2-methoxy-5-bromo-, 1-allyl-2-ethoxy-5-bromo-, 1-allyl-2-n-propoxy-5-bromo-, 1-allyl-2-methylthio-5-bromo-, 1-allyl-2-ethylthio-5-bromo-, 1-allyl-2-n-propylthio-5-bromo-, 1-allyl-2-iso-propylthio-5-bromo-, 1-allyl-2-dimethylamino-5-bromo-, 1-allyl-2-diethylamino-5-bromo-, 1-allyl-2,5-dimethyl-, 1-allyl-2-methoxy-5-methyl-, 1-allyl-2-ethoxy-5-methyl-, 1-allyl-2-n-propoxy-5-methyl-, 1-allyl-2-methylthio-5-methyl-, 1-allyl-2-ethylthio-5-methyl-, 1-allyl-2-n-propylthio-5-methyl-, 1-allyl-2-iso-propylthio-5-methyl-, 1-allyl-2-dimethylamino-5-methyl-, 1-allyl-2-diethylamino-5-methyl-, 1-allyl-2-methyl-5-ethyl-, 1-allyl-2-methoxy-5-ethyl-, 1-allyl-2-ethoxy-5-ethyl-, 1-allyl-2-n-propoxy-5-ethyl-, 1-allyl-2-methylthio-5-ethyl-, 1-allyl-2-ethylthio-5-ethyl-, 1-allyl-2-n-propylthio-5-ethyl-, 1-allyl-2-isopropylthio-5-ethyl-, 1-allyl-2-dimethylamino-5-ethyl- and 1-allyl-2-diethylamino-5-ethyl-1,6-dihydro-4-hydroxy-6-oxo-pyrimidine.

The O-[6-hydroxypyrimidin-4-yl]-(thiono)(thiol)-phosphoric(phosphonic) acid esters and ester-amides (IV) also to be used as starting materials can be prepared in accordance with generally customary processes described in the literature, for example by reacting 4,6-dihydroxy-pyrimidines with (thiono)(thiol)-phosphoric(phosphonic) acid ester halides or ester-amide halides, if appropriate in the presence of acid acceptors and, if appropriate, in the presence of a solvent, in accordance with the following equation:

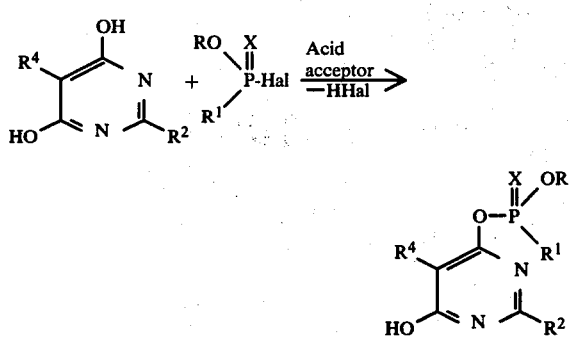

wherein

R, R¹, R², R⁴ and X have the above-mentioned meanings.

The following may be mentioned as individual examples: [6-hydroxy-pyrimidin-4-yl]-, [2-methyl-6-hydroxy-pyrimidin-4-yl]-, [2-ethyl-6-hydroxy-pyrimidin-4-yl]-, [2-n-propyl-6-hydroxy-pyrimidin-4-yl]-, [2-isopropyl-6-hydroxy-pyrimidin-4-yl]-, [2-methoxy-6-hydroxy-pyrimidin-4-yl]-, [2-ethoxy-6-hydroxy-pyrimidin-4-yl]-, [2-n-propoxy-6-hydroxy-pyrimidin-4-yl]-, [2-methylthio-6-hydroxy-pyrimidin-4-yl]-, [2-isopropoxy-6-hydroxy-pyrimidin-4-yl]-, [2-ethylthio-6-hydroxy-pyrimidin-4-yl]-, [2-n-propylthio-6-hydroxy-pyrimidin-4-yl]-, [2-isopropylthio-6-hydroxy-pyrimidin-4-yl]-, [2-dimethylamino-6-hydroxy-pyrimidin-4-yl]-, [2-diethylamino-6-hydroxy-pyrimidin-4-yl]-, [5-methyl-6-hydroxy-pyrimidin-4-yl]-, [5-ethyl-6-hydroxy-pyrimidin-4-yl]-, [5-chloro-6-hydroxy-pyrimidin-4-yl]-, [5-bromo-6-hydroxy-pyrimidin-4-yl]-, [2-methyl-5-chloro-6-hydroxy-pyrimidin-4-yl]-, [2-ethyl-5-chloro-6-hydroxy-pyrimidin-4-yl]-, [2-n-propyl-5-chloro-6-hydroxy-pyrimidin-4-yl]-, [2-isopropyl-5-chloro-6-hydroxy-pyrimidin-4-yl]-, [2-methoxy-5-chloro-6-hydroxy-pyrimidin-4-yl]-, [2-ethoxy-5-chloro-6-hydroxy-pyrimidin-4-yl]-, [2-n-propoxy-5-chloro-6-hydroxy-pyrimidin-4-yl]-, [2-isopropoxy-5-chloro-6-hydroxy-pyrimidin-4-yl]-, [2-methylthio-5-chloro-6-hydroxy-pyrimidin-4-yl]-, 2-ethylthio-5-chloro-6-hydroxy-pyrimidin-4-yl]-, [2-n-propylthio-5-chloro-6-hydroxy-pyrimidin-4-yl]-, [2-isopropylthio-5-chloro-6-hydroxy-pyrimidin-4-yl]-, [2-dimethylamino-5-chloro-6-hydroxy-pyrimidin-4-yl]-, [2-diethylamino-5-chloro-6-hydroxy-pyrimidin-4-yl]-, [2-methyl-5-bromo-6-hydroxy-pyrimidin-4-yl]-, [2-ethyl-5-bromo-6-hydroxy-pyrimidin-4-yl]-, [2-n-propyl-5-bromo-6-hydroxy-pyrimidin-4-yl]-, [2-isopropyl-5-bromo-6-hydroxy-pyrimidin-4-yl]-, [2-methoxy-5-bromo-6-hydroxy-pyrimidin-4-yl]-, [2-ethoxy-5-bromo-6-hydroxy-pyrimidin-4-yl]-, [2-n-propoxy-5-bromo-6-hydroxy-pyrimidin-4-yl]-, [2-isopropoxy-5-bromo-6-hydroxy-pyrimidin-4-yl]-, [2-methylthio-5-bromo-6-hydroxy-pyrimidin-4-yl]-, [2-ethylthio-5-methyl-6-hydroxy-pyrimidin-4-yl]-, [2-n-propylthio-5-methyl-6-hydroxy-pyrimidin-4-yl]-, [2-isopropylthio-5-methyl-6-hydroxy-pyrimidin-4-yl]-, [2-dimethylamino-5-bromo-6-hydroxy-pyrimidin-4-yl]-, [2-diethylamino-5-bromo-6-hydroxy-pyrimidin-4-yl]-, [2,5-dimethyl-6-hydroxy-pyrimidin-4-yl]-, [2-ethyl-5-methyl-6-hydroxy-pyrimidin-4-yl]-, [2-n-propyl-5-methyl-6-hydroxy-pyrimidin-4-yl]-, [2-isopropyl-5-methyl-6-hydroxy-pyrimidin-4-yl]-, [2-methoxy-5-methyl-6-hydroxy-pyrimidin-4-yl]-, [2-ethoxy-5-methyl-6-hydroxy-pyrimidin-4-yl]-, [2-n-propoxy-5-methyl-6-hydroxy-pyrimidin-4-yl]-, [2-isopropoxy-5-methyl-6-hydroxy-pyrimidin-4-yl]-, [2-methylthio-5-methyl-6-hydroxy-pyrimidin-4-yl]-, [2-ethylthio-5-methyl-6-hydroxy-pyrimidin-4-yl]-, [2-n-propylthio-5-methyl-6-hydroxy-pyrimidin-4-yl]-, [2-isopropylthio-5-methyl-6-hydroxy-pyrimidin-4-yl]-, [2-dimethylamino-5-methyl-6-hydroxy-pyrimidin-4-yl]-, [2-diethylamino-5-methyl-6-hydroxy-pyrimidin-4-yl]-, [2-methyl-5-ethyl-6-hydroxy-pyrimidin-4-yl]-, [2,5-diethyl-6-hydroxy-pyrimidin-4-yl]-, [2-n-propyl-5-ethyl-6-hydroxy-pyrimidin-4-yl]-, [2-isopropyl-5-ethyl-6-hydroxy-pyrimidin-4-yl]-, [2-methoxy-5-ethyl-6-hydroxy-pyrimidin-4-yl]-, [2-ethoxy-5-ethyl-6-hydroxy-pyrimidin-4-yl]-, [2-n-propoxy-5-ethyl-6-hydroxy-pyrimidin-4-yl]-, [2-isopropoxy-5-ethyl-6-hydroxy-pyrimidin-4-yl]-, [2-methylthio-5-ethyl-6-hydroxy-pyrimidin-4-yl]-, [2-ethylthio-5-ethyl-6-hydroxy-pyrimidin-4-yl]-, [2-n-propylthio-5-ethyl-6-hydroxy-pyrimidin-4-yl]-, [2-isopropylthio-5-ethyl-6-hydroxy-pyrimidin-4-yl]-, [2-dimethylamino-5-ethyl-6-hydroxy-pyrimidin-4-yl]- and [2-diethylamino-5-ethyl-6-hydroxy-pyrimidin-4-yl]-O,O-dimethyl-, -O,O-diethyl-, -O,O-di-n-propyl-, -O,O-di-isopropyl-, -O,O-di-n-butyl-, -O,O-di-isobutyl-, -O,O-di-sec.-butyl-, -O-methyl-O-ethyl-, -O-methyl-O-n-propyl-, -O-methyl-O-isopropyl-, -O-methyl-O-n-butyl-, -O-methyl-O-isobutyl-, -O-methyl-O-sec.-butyl-, -O-methyl-O-tert.-butyl-, -O-ethyl-O-n-propyl-, -O-ethyl-O-isopropyl-, -O-ethyl-O-n-butyl-, -O-ethyl-O-sec.-butyl-, -O-ethyl-O-isobutyl-, -O-n-propyl-O-butyl- and -O-isopropyl-O-butylthionophosphoric acid ester, and -O,S-dimethyl-, -O,S-diethyl-, -O,S-di-n-propyl-, -O,S-di-isopropyl-, -O,S-di-n-butyl-, -O,S-di-isobutyl-, -O,S-di-tert.-butyl-, -O-ethyl-S-n-propyl-, -O-ethyl-S-isopropyl-, -O-ethyl-S-n-butyl-, -O-ethyl-S-sec.-butyl-, O-n-propyl-S-ethyl-, O-n-propyl-S-isopropyl-, -O-n-butyl-S-n-propyl- and -O-sec.-butyl-S-ethyl-thionothiolphosphoric acid ester, as well as -O-methyl-, -O-ethyl-, -O-n-propyl-, -O-isopropyl-, -O-n-butyl-, -O-iso-butyl-, O-sec.-butyl-, -O-tert.-butyl-methane- and -ethane-, -n-propane-, -isopropane-, -n-butane-, -isobutane-, -tert-butane-, -sec.-butane- and -benzene-thionophosphonic acid ester and -O-methyl-N-methyl-, -O-methyl-N-ethyl-, -O-methyl-N-n-propyl-, -O-methyl-N-isopropyl-, -O-ethyl-N-methyl-, -O-ethyl-N-ethyl-, -O-ethyl-N-n-propyl-, -O-ethyl-N-isopropyl-, -O-n-propyl-N-methyl-, -O-n-propyl-N-ethyl-, -O-n-propyl-N-n-propyl-, -O-n-propyl-N-isopropyl-, -O-isopropyl-N-methyl-. -O-isopropyl-N-ethyl-, -O-isopropyl-N-n-propyl-, -O-isopropyl-N-isopropyl-, -O-n-butyl-N-methyl-, -O-n-butyl-N-ethyl-, -O-n-butyl-N-n-propyl-, -O-n-butyl-N-isopropyl-, -O-tert.-butyl-N-methyl-, -O-tert.-butyl-N-ethyl-, -O-tert.-butyl-N-n-propyl-, -O-tert.-butyl-N-isopropyl-, -O-isobutyl-N-methyl-, -O-isobutyl-N-ethyl-, -O-sec.-butyl-N-methyl and -O-sec.-butyl-N-ethyl-thionophosphoric acid ester-amide.

The following may be mentioned as individual examples of the industrially readily available alkyl halides and alkenyl halides (V): methyl iodide, methyl bromide, ethyl bromide, ethyl iodide, n-propyl bromide, n-butyl bromide, allyl bromide and crotyl bromide.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 10° to 120° C., preferably at from 35° to 60° C.

The reaction is in general allowed to take place under normal pressure.

To carry out process variant (a), the starting materials are preferably employed in equimolar amounts. An excess of one or other reactant produces no significant advantages. The reactants are in general brought together in one of the stated solvents and are stirred for one or more hours, in most cases at an elevated temperature, in order to complete the reaction.

Thereafter an organic solvent, for example toluene, is added to the reaction mixture and the organic phase is worked up in accordance with customary methods, by washing, drying and distilling off the solvent.

In process variant (b), the alkyl halide or alkenyl halide is preferably employed in 10–15% stoichiometric excess. The reaction is carried out, and the mixture worked up, as described for process variant (a).

The new compounds are often obtained in the form of oils which in most cases cannot be distilled without decomposition but can be freed from the last volatile constituents by so-called "slight distillation", that is to say by prolonged heating under reduced pressure to moderately elevated temperatures, and can be purified in this way. They are characterized by the refractive index. Some compounds are obtained in a crystalline form having a sharp melting point.

As already mentioned, the 6-oxo-pyrimidinyl-(thiono)(thiol)-phosphoric(phosphonic) acid esters and ester-amides according to the invention are distinguished by an excellent insecticidal and acaricidal activity. They are active against plant pests, pests harmful to health and pests of stored products and, in the veterinary medicine field, against ectoparasites. They combine a low phytotoxicity with a good action against sucking and biting insects and mites.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating arthropod pests, especially insects and arachnids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example Lepisma saccharina; from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocera gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example, *Hercinothrips femoralis* and *Thrips tabaci,* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kühniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and Costelytra zealandica; from the order of the Hymenoptera, for example Diprion spp., Hoplocampa spp., Lasius spp., *Monomorium pharaonis* and Vespa spp.; from the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., Pegomyia hyoscyami, Ceratitis capitata, Dacus oleae and *Tipula paludosa;* from the order of the Siphonaptera, for example *Xenopsylla cheopis* and Ceratophyllus spp.; from the class of the Arachnida, for example *Scorpio maurus* and Latrodectus mactans; from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., and tetranychus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example in the case where water is used as diluent, organic solvents may be added as auxillary solvents. The following may be chiefly considered for use as conventional carrier vehicles for this purpose: aerosol propellants which are gaseous at normal temperatures and pressures, such as halogenated hydrocarbons, e.g. dichlorodifluoro methane and trichlorofluoro methane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules, crushed and fractionated natural rocks such as calcite, marble, pumice, sepiolite and dolomite, as well as synthetic granules of inorganic and organic meals, and granules of organic material such as sawdust, coconut sheels, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycolethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant-protection agents, such as other insecticides, acaricides, and nematicides, bactericides, rodenticides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat hereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

The 1,6-dihydro-4-hydroxy-6-oxo-pyrimidines to be used as starting materials could be prepared, for example, as follows:

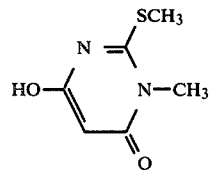
(a)

A mixture of 45 g (0.5 mol) of N-methylthiourea, 54 g (1 mol) of sodium methylate, 200 ml of methanol and 80 g (0.5 mol) of malonic acid diethyl ester was boiled for 3 hours under reflux. 71 g (0.5 mol) of methyl iodide were then added dropwise at about 50° C. and the mixture was stirred for a further 0.5 hour at 50° C. The salt which crystallized out was filtered off and was then dissolved in 400 ml of water. The solution was neutralized by adding glacial acetic acid, the precipitate was then filtered off, and 80 g (93% of theory) of 1,6-dihydro-4-hydroxy-1-methyl-2-methylthio-6-oxo-pyrimidine were thus obtained in the form of a colorless powder of melting point 198° C.

The following compounds of the general formula

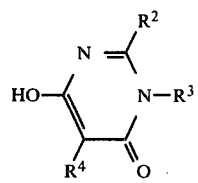
(III)

could be prepared analogously:

Table 1

| $R^2$ | $R^3$ | $R^4$ | Yield (% of theory) | Physical data (refractive index; melting point, °C.) |
|---|---|---|---|---|
| SCH$_3$ | —CH$_2$—CH=CH$_2$ | H | 51 | 176 |
| SCH$_3$ | C$_3$H$_7$-iso | H | 70 | 198 |
| SCH$_3$ | CH$_3$ | CH$_3$ | 82 | 225 |
| SCH$_3$ | CH$_3$ | Cl | | |

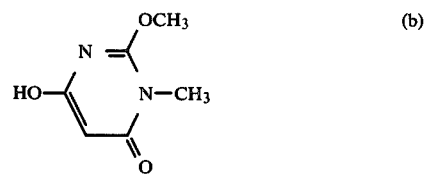
(b)

A mixture of 172 g (1 mol) of 1,6-dihydro-4-hydroxy-1-methyl-2-methylthio-6-oxo-pyrimidine, 700 ml of methanol and 5 ml of a solution of hydrogen chloride in ether was boiled for 10 days under reflux. The reaction mixture was then filtered while still hot and the filtrate is evaporated in vacuo. The residue was triturated with ether and the crystalline product was filtered off. In this way, 71 g (40% of theory) of 1,6-dihydro-4-hydroxy-1-methyl-2-methoxy-6-oxo-pyrimidine were obtained in the form of colorless crystals of melting point 170°–171° C.

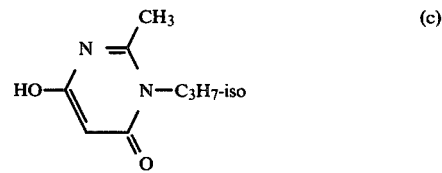
(c)

A solution of 61.8 g (0.5 mol) of acetimido-ethyl ester hydrochloride and 44.2 g (0.75 mol) of isopropylamine in 500 ml of ethanol was stirred for 2 days at room temperature and then evaporated in vacuo. The residue was dissolved in 400 ml of methanol and 54 g (1 mol) of sodium methylate and 80 g (0.5 mol) of malonic acid diethyl ester were added to the solution. The mixture was then boiled for 7 hours under reflux, after which it was concentrated in vacuo. The residue was dissolved in 200 ml of water, concentrated hydrochloric acid was added until a pH value of 5 was reached, and the product which had precipitated was then filtered off. 20 g (24% of theory) of 1-isopropyl-2-methyl-4-hydroxy-6-oxo-1,6-dihydro-pyrimidine were thus obtained in the form of a colorless crystal powder of melting point 245° C. (with decomposition).

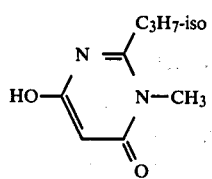
(d)

6 g (0.33 mol) of 1-methyl-2-isopropyl-4-methoxy-6-oxo-1,6-dihydro-pyrimidine (for preparation, see line 15 this page) were dissolved in 30 ml of acetone and converted to the hydrochloride by adding a solution of hydrochloric acid in ether. The salt was filtered off and after drying was warmed for 20 minutes to 150°–155° C. After the elimination of methyl chloride had ceased, the material was cooled, triturated with ether and filtered off. 3.9 g (92% of theory) of 1-methyl-2-isopropyl-4-hydroxy-6-oxo-1,6-dihydro-pyrimidine were thus obtained in the form of a colourless powder of melting point 159° C.

The 1-methyl-2-isopropyl-4-methoxy-6-oxo-1,6-dihydro-pyrimidine to be used as the starting material was prepared as follows:

A mixture of 16.8 g (0.1 mol) of 2-isopropyl-4-methoxy-6-hydroxy-pyrimidine (for its preparation, see German Offenlegungsschrift (German Published Specification) 2,412,903), 15.2 g (0.11 mol) of potassium carbonate, 12.6 g (0.1 mol) of dimethyl sulphate and 200 ml of acetonitrile was stirred for 4 hours at 45° C. The reaction mixture was then filtered and the filtrate was evaporated in vacuo. The residue was triturated with water and filtered off. 10 g (55% of theory) of a colorless powder of melting point 91° C. were thus obtained.

The following compounds of the general formula

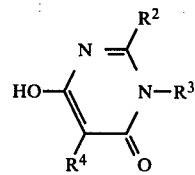

could be prepared analogously to instructions (c) and (d):

Table 2

| $R^2$ | $R^3$ | $R^4$ | Yield (% of theory) | Physical data (refractive index; melting point, °C.) |
|---|---|---|---|---|
| CH$_3$ | CH$_3$ | H | 40 | 135 (with decomposition) (as the Na salt) |
| C$_3$H$_7$-iso | C$_2$H$_5$ | H | 37 | 137 |
| CH$_3$ | C$_2$H$_5$ | H | 8 | 192 (with decomposition) |
| CH$_3$ | C$_3$H$_7$-n | H | 24 | 203 |
| C$_2$H$_5$ | C$_2$H$_5$ | H | 36 | 160 (with decomposition) |
| H | CH$_3$ | H | | |
| C$_2$H$_5$ | CH$_3$ | H | | |

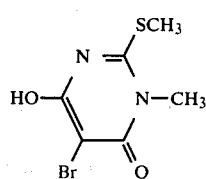
(e)

16 g (0.1 mol) of bromine were added to a solution of 17.2 g (0.1 mol) of 1-methyl-2-methylthio-4-hydroxy-6-oxo-1,6-dihydro-pyrimidine in 110 ml of 1 N sodium hydroxide solution at room temperature. After the end of the addition, the batch was stirred for a further 0.5 hour and was then cooled to 5° C. The product which had precipitated was filtered off and rinsed with water. 18 g (76% of theory) of 1-methyl-2-methylthio-4-hydroxy-5-bromo-6-oxo-1,6-dihydro-pyrimidine were thus obtained in the form of pale yellow crystals of melting point 184° C. (with decomposition).

The compound of the formula

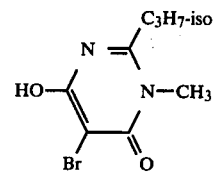

could be obtained analogously in 69% yield, and with a melting point of 198° C. (with decomposition).

The [6-hydroxy-pyrimidin-4-yl]-(thiono)-phosphoric(phosphonic) acid esters also to be used as starting materials could be prepared, for example, as follows:

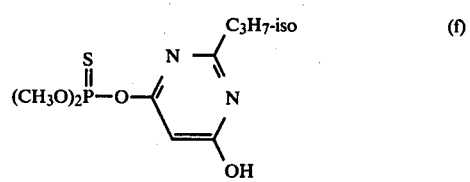
(f)

A mixture of 18.4 g (0.12 mol) of 2-isopropyl-4,6-dihydroxypyrimidine, 12.5 g (0.125 mol) of triethylamine and 60 ml of methylene chloride was stirred for 1 hour at room temperature. It was then cooled to about 5° C. and at this temperature 16 g (0.1 mol) of O,O-dimethylthionophosphoric acid diester chloride were added dropwise. The reaction mixture was then stirred for 20 hours at room temperature, after which it was filtered and the filtrate was evaporated in vacuo. The residue was triturated with water and the crystallized product was filtered off. 22.7 g (82% of theory) of O,O-dimethyl-O-[2-isopropyl-6-hydroxy-pyrimidin-4-yl]-thionophosphoric acid ester were thus obtained in the form of colorless crystals of melting point 123° C.

The following compounds of the general formula

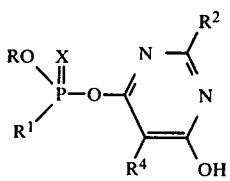

could be prepared analogously:

Table 3

| R | R¹ | R² | R⁴ | X | Yield (% of theory) | Physical data (refractive index; melting point, °C.) |
|---|---|---|---|---|---|---|
| $C_2H_5$ | $OC_2H_5$ | $C_3H_7$-iso | H | S | 98 | 94 |
| $CH_3$ | $OCH_3$ | H | H | S | 9 | 148 |
| $C_2H_5$ | $OC_2H_5$ | $SCH_3$ | H | S | 35 | 110 |
| $C_2H_5$ | $OC_2H_5$ | H | H | S | 26 | 83 |
| $C_3H_7$-iso | $CH_3$ | $C_3H_7$-iso | H | S | 18 | 136 |
| $C_2H_5$ | $C_2H_5$ | $C_3H_7$-iso | H | S | 52 | 88 |
| $C_2H_5$ | $OC_3H_7$-n | $C_3H_7$-iso | H | S | 60 | $n_D^{23}$:1.5168 |
| $C_2H_5$ | $SC_3H_7$-n | $C_3H_7$-iso | H | S | 63 | $n_D^{23}$:1.5479 |
| $C_2H_5$ | 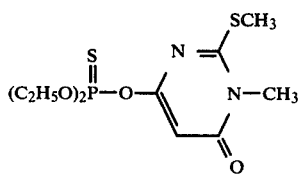 | $C_3H_7$-iso | H | S | 75 | 116 |
| $C_2H_5$ | $OC_2H_5$ | $OC_2H_5$ | H | S | 20 | 101 |
| $C_2H_5$ | $OC_2H_5$ | $C_3H_7$-iso | Br | S | 43 | 117 |
| $C_2H_5$ | $OC_2H_5$ | $N(CH_3)_2$ | H | S | 20 | 132 |
| $C_2H_5$ | $OC_2H_5$ | $CH_3$ | H | S | 7 | 79 |
| $C_2H_5$ | $OC_2H_5$ | 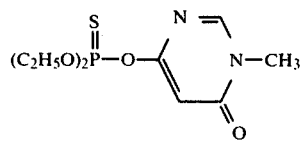 | H | S | 12 | 118 |
| $C_2H_5$ | $OC_2H_5$ | $C_3H_7$-iso | $CH_3$ | S | 48 | 103 |

EXAMPLE 2:

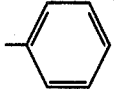  (1)

A mixture of 17.2 g (0.1 mol) of 1,6-dihydro-4-hydroxy-1-methyl-2-methylthio-6-oxo-pyrimidine, 20.7 g (0.15 mol) of potassium carbonate and 18.8 g (0.1 mol) of O,O-diethylthionophosphoric acid diester chloride was stirred for 12 hours at 45° C. The reaction mixture was then poured into 400 ml of toluene and washed twice with 300 ml of water at a time. The toluene solution was dried over sodium sulphate and evaporated in vacuo. The residue was triturated with petroleum ether and the product was filtered off after it had crystallized. In this way, 11.3 g (35% of theory) of O,O-diethyl-O-[1,6-dihydro-1-methyl-2-methylthio-6-oxo-pyrimidin-4-yl]-thionophosphoric acid ester were obtained in the form of colorless crystals of melting point 74° C.

EXAMPLE 3:

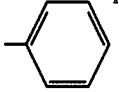  (2)

15.6 g (0.11 mol) of methyl iodide were added to a mixture of 26.4 g (0.1 mol) of O,O-diethyl-O-[6-hydroxy-pyrimidin-4-yl]-thionophosphoric acid ester, 20.7 g (0.15 mol) of potassium carbonate and 300 ml of acetonitrile. The reaction mixture was stirred for a further 3 hours at 45° C. and was then poured into 400 ml of toluene. The toluene solution was washed twice with 300 ml of water at a time and was dried over sodium sulphate. The solvent was then stripped off in vacuo and the residue was subjected to slight distillation. After trituration with petroleum ether, the crystalline product was filtered off. 17 g (62% of theory) of O,O-diethyl-O-[1,6-dihydro-1-methyl-6-oxo-pyrimidin-4-yl]-thionophosphoric acid ester were thus obtained in the form of a colorless powder of melting point 66° C.

The following compounds of the general formula

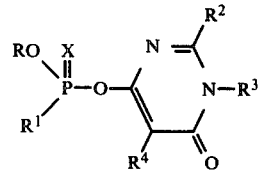  (I)

could be prepared analogously to Examples 2 and 3.

Table 4

| Compound No. | R | R¹ | R² | R³ | R⁴ | X | Yield (% of theory) | Physical data (refractive index; melting point, °C.) |
|---|---|---|---|---|---|---|---|---|
| 3 | $C_3H_7$-iso | $CH_3$ | $C_3H_7$-iso | $CH_3$ | H | S | 62 | $N_D^{26}$:1.5253 |
| 4 | $C_2H_5$ | $OC_2H_5$ | $C_3H_7$-iso | $CH_3$ | H | S | 73 | $n_D^{23}$:1.5150 |
| 5 | $C_3H_7$-iso | $CH_3$ | $SCH_3$ | $CH_3$ | H | S | 53 | 94 |
| 6 | $C_2H_5$ | $C_2H_5$ | $SCH_3$ | $CH_3$ | H | S | 55 | $n_D^{21}$:1.5713 |

Table 4-continued

| Compound No. | R | R¹ | R² | R³ | R⁴ | X | Yield (% of theory) | Physical data (refractive index; melting point, °C.) |
|---|---|---|---|---|---|---|---|---|
| 7 | $C_2H_5$ |  (benzene) | $SCH_3$ | $CH_3$ | H | S | 65 | 87 |
| 8 | $C_2H_5$ | $SC_3H_7$-n | $SCH_3$ | $CH_3$ | H | S | 41 | $n_D^{22}$: 1.5684 |
| 9 | $C_2H_5$ | $OC_2H_5$ | $CH_3$ | $C_3H_7$-iso | H | S | 50 | $n_D^{22}$: 1.5162 |
| 10 | $C_2H_5$ | $OC_3H_7$-n | $C_3H_7$-iso | $CH_3$ | H | S | 75 | $n_D^{22}$: 1.5153 |
| 11 | $C_2H_5$ | $SC_3H_7$-n | $C_3H_7$-iso | $CH_3$ | H | S | 79 | $n_D^{22}$: 1.5457 |
| 12 | $C_2H_5$ | (benzene) | $C_3H_7$-iso | $CH_3$ | H | S | 84 | $n_D^{22}$: 1.5740 |
| 13 | $C_2H_5$ | $C_2H_5$ | $C_3H_7$-iso | $CH_3$ | H | S | 90 | $n_D^{22}$: 1.5302 |
| 14 | $C_2H_5$ | $OC_2H_5$ | $OCH_3$ | $CH_3$ | H | S | 37 | 54 |
| 15 | $C_2H_5$ | $C_2H_5$ | $OCH_3$ | $CH_3$ | H | S | 79 | $n_D^{20}$: 1.5449 |
| 16 | $CH_3$ | $OCH_3$ | $OCH_3$ | $CH_3$ | H | S | 61 | $n_D^{21}$: 1.5459 |
| 17 | $C_2H_5$ | $NH-C_3H_7$-iso | $SCH_3$ | $CH_3$ | H | S | 6 | 91 |
| 18 | $C_2H_5$ | $NH-C_3H_7$-iso | $SCH_3$ | $CH_3$ | H | O | 60 | 39 |
| 19 | $C_2H_5$ | $OC_2H_5$ | $C_3H_7$-iso | $CH_3$ | H | O | 54 | $n_D^{18}$: 1.4882 |
| 20 | $C_2H_5$ | $OC_2H_5$ | $CH_3$ | $CH_3$ | H | S | 55 | 42 |
| 21 | $C_2H_5$ | $C_2H_5$ | $CH_3$ | $CH_3$ | H | S | 25 | 84 |
| 22 | $CH_3$ | $OCH_3$ | $CH_3$ | $CH_3$ | H | S | 30 | $n_D^{20}$: 1.5437 |
| 23 | $CH_3$ | $OCH_3$ | $C_3H_7$-iso | $CH_3$ | H | S | 23 | $n_D^{22}$: 1.5322 |
| 24 | $C_2H_5$ | $OC_2H_5$ | $CH_3$ | $C_2H_5$ | H | S | 71 | $n_D^{22}$: 1.5140 |
| 25 | $C_2H_5$ | $OC_2H_5$ | $SCH_3$ | $-CH_2-CH=CH_2$ | H | S | 62 | $n_D^{22}$: 1.5566 |
| 26 | $C_2H_5$ | $C_2H_5$ | $SCH_3$ | $-CH_2-CH=CH_2$ | H | S | 68 | $n_D^{22}$: 1.5721 |
| 27 | $C_2H_5$ | $OC_2H_5$ | $SCH_3$ | $C_3H_7$-iso | H | S | 68,2 | $n_D^{24}$: 1.5485 |
| 28 | $CH_3$ | $OCH_3$ | $SCH_3$ | $C_3H_7$-iso | H | S | 74 | $n_D^{24}$: 1.5349 |
| 29 | $C_2H_5$ | $C_2H_5$ | $SCH_3$ | $C_3H_7$-iso | H | S | 67,5 | $n_D^{24}$: 1.5486 |
| 30 | $C_2H_5$ | $OC_2H_5$ | $SCH_3$ | $CH_3$ | Br | S | 51 | 60 |
| 31 | $CH_3$ | $OCH_3$ | $SCH_3$ | $CH_3$ | Br | S | 32 | 76 |
| 32 | $CH_3$ | $OCH_3$ | $CH_3$ | $C_3H_7$-iso | H | S | 64 | 41 |
| 33 | $C_2H_5$ | $OC_2H_5$ | $SCH_3$ | $CH_3$ | $CH_3$ | S | 63 | 64 |
| 34 | $CH_3$ | $OCH_3$ | $SCH_3$ | $CH_3$ | $CH_3$ | S | 63 | 62 |
| 35 | $CH_3$ | $CH_3$ | $C_2H_5$ | $C_2H_5$ | H | S | 73 | 54 |
| 36 | $C_2H_5$ | $OC_2H_5$ | $SCH_3$ | $CH_3$ | Cl | S | | |
| 37 | $C_2H_5$ | $OC_2H_5$ | $C_3H_7$-iso | $CH_3$ | Br | S | 45 | $n_D^{22}$: 1.5402 |
| 38 | $CH_3$ | $OCH_3$ | H | $CH_3$ | H | S | | |
| 39 | $C_2H_5$ | $OC_2H_5$ | $C_2H_5$ | $CH_3$ | H | S | 92 | $n_D^{24}$: 1.5216 |
| 40 | $CH_3$ | $OCH_3$ | $C_2H_5$ | $CH_3$ | H | S | | |
| 41 | $C_2H_5$ | $OC_2H_5$ | $C_2H_5$ | $C_2H_5$ | H | S | 76 | $n_D^{28}$: 1.5212 |
| 42 | $C_2H_5$ | $OC_2H_5$ | $C_3H_7$-n | $CH_3$ | H | S | 80 | 47 |
| 43 | $C_2H_5$ | $OC_2H_5$ | $CH_3$ | $C_3H_7$-n | H | S | 82 | $n_D^{19}$: 1.5215 |
| 44 | $C_2H_5$ | $OC_2H_5$ | $N(CH_3)_2$ | $CH_3$ | H | S | 59 | $n_D^{24}$: 1.5442 |
| 45 | $C_2H_5$ | $C_2H_5$ | $N(CH_3)_2$ | $CH_3$ | H | S | 77 | $n_D^{24}$: 1.5560 |
| 46 | $CH_3$ | $OCH_3$ | $N(CH_3)_2$ | $CH_3$ | H | S | 46 | $n_D^{24}$: 1.5622 |
| 47 | $C_2H_5$ | $OC_2H_5$ | $N(C_2H_5)_2$ | $CH_3$ | H | S | | |
| 48 | $CH_3$ | $OCH_3$ | $N(C_2H_5)_2$ | $CH_3$ | H | S | | |
| 49 | $CH_3$ | $OCH_3$ | $OCH_3$ | $C_3H_7$-iso | H | S | 74 | 48 |
| 50 | $C_2H_5$ | $OC_2H_5$ | $OCH_3$ | $C_3H_7$-iso | H | S | 70 | $n_D^{24}$: 1.5116 |
| 51 | $C_2H_5$ | $CH_3$ | $SCH_3$ | $C_3H_7$-iso | H | S | 94 | $n_D^{23}$: 1.5558 |
| 52 | $CH_3$ | $OCH_3$ | $SC_3H_7$-iso | $CH_3$ | H | S | 80 | 75 |
| 53 | $C_2H_5$ | $OC_2H_5$ | $SC_3H_7$-iso | $CH_3$ | H | S | 70 | 65 |
| 54 | $CH_3$ | $CH_3$ | $OCH_3$ | $C_3H_7$-iso | H | S | 53 | $n_D^{21}$: 1.5359 |
| 55 | $C_2H_5$ | $SC_3H_7$ | $SCH_3$ | $C_3H_7$-iso | H | S | 98 | $n_D^{23}$: 1.5622 |
| 56 | $C_3H_7$-iso | $CH_3$ | $SCH_3$ | $C_3H_7$-iso | H | S | 91 | $n_D^{23}$: 1.5229 |
| 57 | $C_2H_5$ | $OC_3H_7$-n | $SCH_3$ | $-CH_2-CH=CH_2$ | H | S | 35 | $n_D^{22}$: 1.5521 |
| 58 | $C_2H_5$ | $SC_3H_7$-n | $SCH_3$ | $-CH_2-CH=CH_2$ | H | S | 56 | $n_D^{22}$: 1.5790 |
| 59 | $CH_3$ | $OCH_3$ | $SCH_3$ | $-CH_2-CH=CH_2$ | H | S | 64 | $n_D^{22}$: 1.5750 |
| 60 | $C_2H_5$ | $OC_2H_5$ | H | $C_2H_5$ | H | S | 61 | 57 |
| 61 | $CH_3$ | $C_2H_5$ | $OCH_3$ | $C_3H_7$-iso | H | S | 81 | $n_D^{23}$: 1.5309 |
| 62 | $C_2H_5$ | $NH-C_3H_7$-iso | $C_2H_5$ | $C_2H_5$ | H | S | 54 | 90 |
| 63 | $C_2H_5$ | $NH-C_3H_7$-iso | $C_2H_5$ | $C_2H_5$ | H | O | 32 | $n_D^{22}$: 1.5084 |
| 64 | $C_2H_5$ | $NH-C_3H_7$-iso | $OCH_3$ | $C_3H_7$-iso | H | O | 54 | $n_D^{22}$: 1.5029 |
| 65 | $C_2H_5$ | $SC_3H_7$-n | $OCH_3$ | $C_3H_7$iso | H | O | 77 | $n_D^{22}$: 1.5188 |
| 66 | $C_2H_5$ | $SC_3H_7$-n | $C_2H_5$ | $C_2H_5$ | H | O | 57 | $n_D^{21}$: 1.5240 |
| 67 | $C_2H_5$ | $S_3H_7$-n | $SC_3H_7$-iso | $CH_3$ | H | O | 54 | $n_D^{21}$: 1.5466 |
| 68 | $C_2H_5$ | $SC_3H_7$-n | $SCH_3$ | $CH_3$ | H | O | 65 | $n_D^{21}$: 1.5614 |
| 69 | $C_2H_5$ | $SC_3H_7$-n | $C_3H_7$-iso | $CH_3$ | H | O | 52 | $n_D^{21}$: 1.5203 |
| 70 | $C_2H_5$ | $OC_2H_5$ | $OC_2H_5$ | $CH_3$ | H | S | | |
| 71 | $CH_3$ | $OCH_3$ | $OC_2H_5$ | $CH_3$ | H | S | | |
| 72 | $C_2H_5$ | $OC_2H_5$ | $OC_2H_5$ | $C_2H_5$ | H | S | | |
| 73 | $CH_3$ | $OCH_3$ | $OC_2H_5$ | $C_2H_5$ | H | S | | |
| 74 | $C_2H_5$ | $OC_2H_5$ | $OC_2H_5$ | $C_3H_7$-iso | H | S | | |
| 75 | $CH_3$ | $OCH_3$ | $OC_2H_5$ | $C_3H_7$-iso | H | S | | |

EXAMPLE 4

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamond-back moth (Plutella maculipennis).

After the specified periods of time, the degree of destruction was determined as a percentage: 100% meant that all the caterpillars were killed whereas 0% meant that none of the caterpillars were killed.

The active compounds, the concentrations of the active compounds, the evaluation times and the results can be seen from the following table:

Table 5

| (Plutella Test) | | |
|---|---|---|
| Active compound | Active compound concentration in % | Degree of destruction in % after 3 days |
| $CH_3S-\underset{N=}{\overset{N-}{\diagdown}}\underset{CH_3}{\diagup}$ with $O-P(OC_2H_5)_2$, $\overset{S}{\|}$ (known) (A) | 0.1 | 100 |
| | 0.01 | 0 |
| (2) | 0.1 | 100 |
| | 0.01 | 100 |
| (22) | 0.1 | 100 |
| | 0.01 | 100 |
| (20) | 0.1 | 100 |
| | 0.01 | 100 |
| (21) | 0.1 | 100 |
| | 0.01 | 100 |
| (9) | 0.1 | 100 |
| | 0.01 | 100 |
| (19) | 0.1 | 100 |
| | 0.01 | 100 |
| (4) | 0.1 | 100 |
| | 0.01 | 100 |
| (13) | 0.1 | 100 |
| | 0.01 | 100 |
| (3) | 0.1 | 100 |
| | 0.01 | 100 |
| (10) | 0.1 | 100 |
| | 0.01 | 100 |
| (11) | 0.1 | 100 |
| | 0.01 | 100 |
| (12) | 0.1 | 100 |
| | 0.01 | 100 |
| (16) | 0.1 | 100 |
| | 0.01 | 100 |
| (14) | 0.1 | 100 |
| | 0.01 | 100 |
| (15) | 0.1 | 100 |
| | 0.01 | 100 |
| (1) | 0.1 | 100 |
| | 0.01 | 100 |
| (6) | 0.1 | 100 |
| | 0.01 | 100 |
| (5) | 0.1 | 100 |
| | 0.01 | 100 |
| (8) | 0.1 | 100 |
| | 0.01 | 100 |

Table 5-continued

| (Plutella Test) | | |
|---|---|---|
| Active compound | Active compound concentration in % | Degree of destruction in % after 3 days |
| (18) | 0.1 | 100 |
| | 0.01 | 100 |
| (25) | 0.1 | 100 |
| | 0.01 | 100 |
| (26) | 0.1 | 100 |
| | 0.01 | 100 |
| (24) | 0.1 | 100 |
| | 0.01 | 100 |
| (23) | 0.1 | 100 |
| | 0.01 | 100 |
| (32) | 0.1 | 100 |
| | 0.01 | 100 |
| (43) | 0.1 | 100 |
| | 0.01 | 100 |
| (31) | 0.1 | 100 |
| | 0.01 | 100 |
| (28) | 0.1 | 100 |
| | 0.01 | 100 |
| (27) | 0.1 | 100 |
| | 0.01 | 100 |
| (30) | 0.1 | 100 |
| | 0.01 | 90 |
| (29) | 0.1 | 100 |
| | 0.01 | 100 |
| (41) | 0.1 | 100 |
| | 0.01 | 100 |
| (37) | 0.1 | 100 |
| | 0.01 | 100 |
| (49) | 0.1 | 100 |
| | 0.01 | 100 |
| (50) | 0.1 | 100 |
| | 0.01 | 100 |
| (51) | 0.1 | 100 |
| | 0.01 | 100 |
| (35) | 0.1 | 100 |
| | 0.01 | 100 |
| (42) | 0.1 | 100 |
| | 0.01 | 100 |
| (52) | 0.1 | 100 |
| | 0.01 | 100 |
| (53) | 0.1 | 100 |
| | 0.01 | 100 |
| (46) | 0.1 | 100 |
| | 0.01 | 100 |
| (44) | 0.1 | 100 |
| | 0.01 | 100 |

EXAMPLE 5

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (Tetranychus urticae) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from the following table:

Table 6

*(Tetranychus Test)*

| Active compound | Active compound concentration in % | Degree of destruction in % after 2 days |
|---|---|---|
| (A) (known) $CH_3S-\underset{N}{\overset{N}{\bigvee}}-O-\overset{S}{\underset{\|}{P}}(OC_2H_5)_2$, with $CH_3$ | 0.1 | 0 |
| (B) (known) iso-$C_3H_7-\underset{N}{\overset{N}{\bigvee}}-O-\overset{S}{\underset{\|}{P}}(OC_2H_5)_2$, with $CH_3$ | 0.1 | 95 |
|  | 0.01 | 0 |
| (2) | 0.1 | 100 |
|  | 0.01 | 100 |
| (20) | 0.1 | 100 |
|  | 0.01 | 100 |
| (21) | 0.1 | 100 |
|  | 0.01 | 100 |
| (9) | 0.1 | 100 |
|  | 0.01 | 100 |
| (19) | 0.1 | 100 |
|  | 0.01 | 90 |
| (4) | 0.1 | 100 |
|  | 0.01 | 100 |
| (13) | 0.1 | 100 |
|  | 0.01 | 100 |
| (3) | 0.1 | 100 |
|  | 0.01 | 100 |
| (10) | 0.1 | 100 |
|  | 0.01 | 100 |
| (11) | 0.1 | 100 |
|  | 0.01 | 95 |
| (16) | 0.1 | 100 |
|  | 0.01 | 100 |
| (14) | 0.1 | 100 |
|  | 0.01 | 100 |
| (15) | 0.1 | 100 |
|  | 0.01 | 100 |
| (6) | 0.1 | 100 |
|  | 0.01 | 100 |
| (5) | 0.1 | 100 |
|  | 0.01 | 99 |
| (25) | 0.1 | 100 |
|  | 0.01 | 98 |
| (26) | 0.1 | 100 |
|  | 0.01 | 95 |
| (24) | 0.1 | 100 |
|  | 0.01 | 100 |
| (23) | 0.1 | 100 |
|  | 0.01 | 99 |
| (32) | 0.1 | 100 |
|  | 0.01 | 100 |
| (43) | 0.1 | 100 |
|  | 0.01 | 100 |
| (28) | 0.1 | 100 |
|  | 0.01 | 90 |
| (27) | 0.1 | 98 |
|  | 0.01 | 90 |
| (41) | 0.1 | 100 |
|  | 0.01 | 100 |
| (49) | 0.1 | 100 |
|  | 0.01 | 100 |
| (50) | 0.1 | 100 |
|  | 0.01 | 100 |
| (51) | 0.1 | 100 |
|  | 0.01 | 100 |
| (35) | 0.1 | 100 |
|  | 0.01 | 99 |
| (42) | 0.1 | 100 |
|  | 0.01 | 100 |
| (52) | 0.1 | 100 |
|  | 0.01 | 100 |
| (53) | 0.1 | 100 |
|  | 0.01 | 90 |

EXAMPLE 6

Mosquito larvae test

Test insects: Aëdes aegypti larvae
Solvent: 99 parts by weight of acetone
Emulsifier: 1 part by weight of benzyl hydroxydiphenyl polyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% meant that all the larvae were killed. 0% meant that no larvae at all were killed.

The active compounds, the concentrations of the active compounds and the results can be seen from the following table:

Table 7

*(Mosquito larve test)*

| Active compound | Active compound concentration of the solution in ppm | Degree of destruction in % |
|---|---|---|
| (known) (B) iso-$C_3H_7-\underset{N}{\overset{N}{\bigvee}}-O-\overset{S}{\underset{\|}{P}}(OC_2H_5)_2$, with $CH_3$ | 10 | 100 |
|  | 1 | 0 |
| (3) | 1 | 100 |
| (4) | 0.1 | 100 |
| (1) | 1 | 100 |
| (6) | 1 | 100 |
| (8) | 1 | 100 |
| (43) | 1 | 100 |
| (10) | 1 | 100 |
| (11) | 1 | 100 |
| (13) | 1 | 100 |
| (14) | 1 | 100 |
| (15) | 1 | 100 |
| (16) | 1 | 100 |
| (19) | 1 | 100 |
| (2) | 1 | 100 |
| (20) | 1 | 100 |
| (26) | 1 | 100 |
| (25) | 1 | 100 |
| (23) | 1 | 100 |

EXAMPLE 7

Root-systemic action I

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount by weight of active compound per unit volume of soil, which is given hereinafter in ppm (=mg/liter) was decisive. The treated soil was filled into pots and these were planted with cabbage (*Brassica oleracea*). The active compound could in this way be absorbed from the soil by the roots of the plants and be transported into the leaves.

In order to demonstrate the root-systemic effect, exclusively the leaves were infested with the abovementioned test insects after 7 days. After a further 2 days, the evaluation is carried out by counting or estimating the dead insects. The root-systemic action of the active compound was derived from the mortality figures. It was 100% if all the test insects had been killed and 0% if just as many test insects survived as in the case of the untreated control.

The active compounds, the amounts used and the results can be seen from the table which follows:

Table 8

Root-systemic actionI
*(Myzus persicae)*

| Active compound | Degree of destruction in % at an active compound concentration of 20 ppm |
|---|---|
| 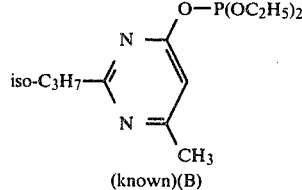 (known)(B) | 0 |
| (4) | 100 |
| (9) | 100 |
| (14) | 100 |
| (2) | 100 |
| (20) | 100 |
| (21) | 100 |
| (24) | 100 |

EXAMPLE 8

Root-systemic action II

Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount by weight of active compound per unit volume of soil, which is given hereinafter in ppm (=mg/liter) was decisive. The treated soil was filled into pots and these were planted with cabbage (*Brassica oleracea*). The active compound could in this way be absorbed from the soil by the roots of the plants and be transported into the leaves.

In order to demonstrate the root-systemic effect, exclusively the leaves were infested with the abovementioned test insects after 7 days. After a further 2 days, the evaluation was carried out by counting or estimating the dead insects. The root-systemic action of the active compound was derived from the mortality figures. It was 100% if all the test insects had been killed and 0% if just as many test insects survived as in the case of the untreated control.

The active compounds, the amounts used and the results can be seen from the table which follows:

Table 9

Root-systemic action II
*(Phaedon cochleariae larvae)*

| Active concentration | Degree of destruction in % at an active compound concentratin of 20 ppm |
|---|---|
| 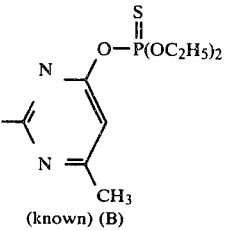 (known) (B) | 0 |
| (9) | 100 |
| (14) | 100 |
| (2) | 100 |
| (20) | 100 |
| (24) | 100 |

EXAMPLE 9

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation had been completely avoided; it was 0% when the infestation was exactly the same as in the case of the control plants in untreated soil which had been infested in the same manner.

The active compound, the amounts applied and the results can be seen from the following table:

Table 10

| Active compound | (*Meloidogyne incognita*) Degree of destruction in % at an active compound concentration of 5 ppm |
|---|---|
| 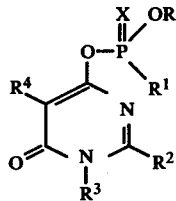 (known) (B) | 0 |
| (4) | 100 |
| (9) | 100 |
| (10) | 100 |
| (11) | 100 |
| (12) | 100 |
| (17) | 100 |
| (20) | 100 |

It will be appreciated that the instant specification and examples are set forth by way of illustration and not limitation, and that various modifications and changes may be made without departing from the spirit and scope of the present invention.

What is claimed:

1. An O-alkyl-O-[1,6-dihydro-substituted-6-oxo-pyrimidin-4-yl]-(thiono)(thiol)-phosphoric (phosphonic) acid ester or ester amide of the formula $$\begin{array}{c} X \quad OR \\ \parallel \diagup \\ O-P \\ \mid \quad \diagdown R^1 \\ R^4 \diagup \diagdown N \\ \parallel \quad \parallel \\ O \diagdown N \diagup R^2 \\ \mid \\ R^3 \end{array}$$

in which
R represents alkyl with 1 to 4 carbon atoms,
$R^1$ represents alkyl with 1 to 3 carbon atoms, alkoxy with 1 to 4 carbon atoms, alkylthio with 1 to 4 carbon atoms, alkylamino with 1 to 4 carbon atoms, or phenyl,
$R^2$ represents hydrogen, alkyl with 1 to 4 carbon atoms, alkoxy with 1 to 3 carbon atoms, alkylthio with 1 to 3 carbon atoms or alkylamino with 1 to 3 carbon atoms,
$R^3$ represents alkyl or alkenyl with up to 4 carbon atoms,
$R^4$ represents hydrogen, methyl, ethyl or halogen, and
X represents oxygen or sulphur.

2. A compound according to claim 1, in which R is alkyl with 1 to 4 carbon atoms, $R^1$ is phenyl, alkyl with 1 to 3 carbon atoms or alkoxy, alkylthio or monoalkylamino each with 1 to 4 carbon atoms, $R^3$ is alkyl or alkenyl with up to 4 carbon atoms, $R^4$ is hydrogen, chlorine, bromine, methyl or ethyl, and X represents sulphur.

3. The compound according to claim 1 wherein such compound is O,O-diethyl-O-[1,6-dihydro-1-methyl-2-isopropyl-6-oxo-pyrimidin-4-yl]-thionophosphoric acid ester of the formula

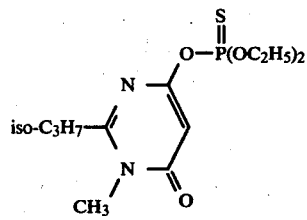

4. The compound according to claim 1 wherein such compound is O,O-diethyl-O-[1,6-dihydro-1-methyl-2-methoxy-6-oxo-pyrimidin-4-yl]-thionophosphoric acid ester of the formula

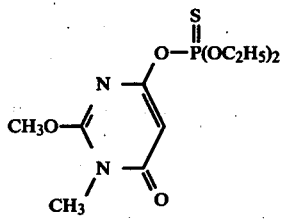

5. The compound according to claim 1 wherein such compound is O,O-dimethyl-O-[1,6-dihydro-1-methyl-2-methoxy-6-oxo-pyrimidin-4-yl]-thionophosphoric acid ester of the formula

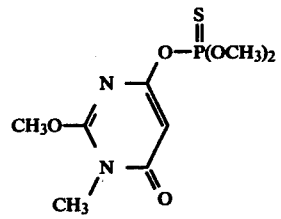

6. The compound according to claim 1 wherein such compound is O,O-diethyl-O-[1,6-dihydro-1-allyl-2-methylthio-6-oxo-pyrimidin-4-yl]-thionophosphoric acid ester of the formula

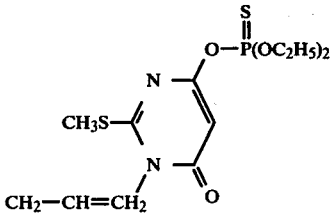

7. The compound according to claim 1 wherein such compound is O,O-dimethyl-O-[1,6-dihydro-1,2-diethyl-6-oxo-Pyrimidin-4-yl]-thiono-phosphoric acid ester of the formula

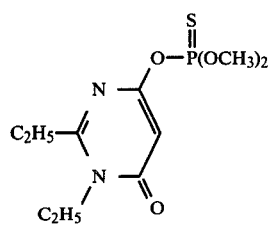

8. An arthropodicidal or nematicidal composition containing as active ingredient an arthropodicidally or nematicidally effect amount of a compound according to claim 1 in admixture with a diluent.

9. A method of combating arthropods or nematodes which comprises applying to the arthropods, nematodes or to a habitat thereof, an arthropodicidally or nematicidally effective amount of a compound according to claim 1.

10. The method according to claim 9 wherein such compound is O,O-diethy-O-[1,6-dihydro-1-methyl-2-isopropyl-6-oxo-pyrimidin-4-yl]-thionophosphoric acid ester, O,O-diethyl-O-[1,6-dihydro-1-methyl-2-methoxy-6-oxo-pyrimidin-4-yl]-thionophosphoric acid ester, O,O-dimethyl-O-[1,6-dihydro-1-methyl-2-methoxy-6-oxo-pyrimidin-4-yl]-thionophosphoric acid ester, O,O-diethyl-O-[1,6-dihydro-1-allyl-2-methylthio-2-oxo-pyrimidin-4-yl]-thionophosphoric acid ester, or O.O-dimethyl-O-[1,6-dihydro-1,2-diethyl-6-oxo-pyrimidin-4-yl]-thiono-phosphoric acid ester.

* * * * *

UNITED STATES PATENT AND TRADEMARK OFFICE
CERTIFICATE OF CORRECTION

PATENT NO. : 4,152,426
DATED : May 1, 1979
INVENTOR(S) : Fritz Maurer

It is certified that error appears in the above—identified patent and that said Letters Patent are hereby corrected as shown below:

Column 27, Line 64-65    Delete "R is alkyl with 1 to 4 carbon atoms,".

Column 27, Line 67-68    Delete "$R_3$ is alkyl or alkenyl with up to 4 carbon atoms,".

Signed and Sealed this

Twenty-sixth Day of May 1981

[SEAL]

Attest:

RENE D. TEGTMEYER

Attesting Officer    Acting Commissioner of Patents and Trademarks